(12) United States Patent
Golz-Berner et al.

(10) Patent No.: US 6,302,950 B1
(45) Date of Patent: Oct. 16, 2001

(54) AQUEOUS SHELLAC SOLUTION OR DISPERSION

(75) Inventors: Karin Golz-Berner; Leonhard Zastrow, both of Monaco (MC)

(73) Assignee: Lancaster Group GmbH, Mainz (DE)

( * ) Notice: Subject to any disclaimer, the term of this patent is extended or adjusted under 35 U.S.C. 154(b) by 0 days.

(21) Appl. No.: 09/463,875
(22) PCT Filed: Jul. 21, 1998
(86) PCT No.: PCT/DE98/02088
§ 371 Date: Jan. 31, 2000
§ 102(e) Date: Jan. 31, 2000
(87) PCT Pub. No.: WO99/06488
PCT Pub. Date: Feb. 11, 1999

(30) Foreign Application Priority Data

Aug. 1, 1997 (DE) .............................................. 197 34 548

(51) Int. Cl.$^7$ .................................................. C09D 193/02
(52) U.S. Cl. .................. 106/238; 106/162.2; 106/203.3; 106/205.4; 524/77
(58) Field of Search .............................. 106/162.2, 203.3, 106/205.4, 238; 524/77

(56) References Cited

U.S. PATENT DOCUMENTS

| | | |
|---|---|---|
| 2,834,770 | 5/1958 | Kalkhof-Rose . |
| 3,261,705 | 7/1966 | Gallagher . |
| 3,276,870 | 10/1966 | Bitting et al. . |
| 4,071,645 * | 1/1978 | Kahn ..................................... 427/340 |
| 4,496,675 | 1/1985 | Hille et al. . |
| 5,194,464 * | 3/1993 | Itoh et al. .............................. 524/42 |
| 5,567,438 | 10/1996 | Cook . |

FOREIGN PATENT DOCUMENTS

WO96/41613   12/1996   (WO) .

* cited by examiner

*Primary Examiner*—David Brunsman
(74) *Attorney, Agent, or Firm*—Collard & Roc, P.C.

(57) ABSTRACT

The invention relates to an aqueous solution or dispersion with high shellac content. The aqueous shellac solution or dispersion is characterized in that it has a pH value of 2 to 4.2, and contains: 1 to 60% wt. shellac; 0.1 to 3% wt. of at least one water-soluble film former; 0.1 to 1% wt. of at least acid-resistant gel former; and water bringing the total to 100% wt. In accordance with the invention, the solution is produced by the following method: particle-shaped shellac is added to an aqueous solution and homogenized by stirring at 10 to 1500 rev/min., at a temperature of 5 to 20° C. The aqueous solution has a pH value of 2 to 4.2 and contains at least one water-soluble film former and at least one acid-resistant gel former. The shellac solution or dispersion can be used in the paint and varnish industry, the food industry and in cosmetics.

14 Claims, No Drawings

AQUEOUS SHELLAC SOLUTION OR DISPERSION

The invention relates to an aqueous solution or dispersion with high shellac content.

Shellac is a natural resin excreted by the female lac insect Kerria lacca. The purified wax-free resin, used in the production of cosmetics, has a molecular weight of approx. 1000. It comprises a number of hydroxymonodicarboxylic acids in the form of lactones, lactides and intramolecular esters. The principal components are aleuritic acid, shellolic acid and jalaric acid ($C_{15}H_{20}O_5$) with molecular weights of 304, 296 and 280 respectively. Shellac is thus rather an oligomere of hyroxycarboxylic acids than a polymer. By means of a solvent extraction method, e.g. using an alcohol, impurities can be removed and after decolouration with active carbon and evaporation of the alcohol, shellac can be transformed into a yellowish to faintly yellowish solid.

From WO96/41613 the use of shellac as a separating agent between the separate layers in a sunscreen agent comprised of three or more layers is known, so that a multilayer structure of the sunscreen agent forms on the skin and the skin contacts only that layer which contains skin-tolerant inorganic sunscreen agents.

Aqueous shellac solutions or dispersions have hitherto been unknown.

It is thus the object of the invention to develop aqueous solutions or dispersions with shellac, in particular solutions or dispersions with shellac contents and viscosities exceeding approx. 200 cP.s.

The invention provides for an aqueous shellac solution or dispersion, characterised by a content of:

Shellac of 1 to 60% wt;

at least one water-soluble film former of 0.1 to 3% wt;

at least one acid-resistant gel former of 0.1 to 1% wt;

water to 100%; and a pH value of 2 to 4.2.

All percentage information relates to the weight (mass) of the total dispersion or solution.

Particularly preferred contents of shellac range from 10 to 50% wt; preferably 15 to 50% wt and in particular 20 to 40% wt.

The shellac solution or dispersion is only resistant in acid, in particular in the pH range of between 2 and 3.5. Setting the pH value can take place with any inorganic or organic acid or a strongly acidic salt, for example with citric acid. However, the choice of acid or salt should match the intended application of the shellac.

The invention also covers a method for producing aqueous shellac solutions or dispersions according to the following method: particle-shaped shellac is added to an aqueous solution and homogenised by stirring at 10 to 1,500 rev/min at a temperature of 5 to 20° C. Said aqueous solution has a pH value of 2 to 4.2 and contains at least one water-soluble film former and at least one acid-resistant gel former.

The new shellac solutions are present at a shellac content of up to approx. 30% wt and in this region comprise viscosities up to approx. 2,500 Mpa·s. For example, the viscosity of a 10% shellac solution is approx. 500 Mpa·s the viscosity of a 20% shellac solution is approx. 1,000 Mpa·s.

Above approx. 30% shellac, aqueous dispersions result with good dispersibility of the particle-shaped shellac, up to approx. 60% wt.

Shellac solutions can be transformed to a dispersion by adding e.g. phospholipids, so that dispersions can also be present in the entire range claimed.

A pH value of approx. 2 to 4.2 and matching of the surface tension of the component to be introduced to the surface tension of water, are essential in the production of the dispersion and the solution of shellac in water.

Preferably a polyvinyl pyrrolidone is used as a water-soluble film former, e.g. PCPK30®. Further possible film formers include chitosan, microcrystalline chitosan, quarternary chitosan, polymers of the acrylic acid series, quarternary cellulose derivatives, hyaluronic acid and their salts.

The acid-resistant gel former can for example be a modified natural polysaccharid such as guar hydroxypropyl-trinonium chloride (CTFA name) (Jaguar C14S®). Other possible gel formers include agar, alginates or alginic acid.

Mixtures of several film formers and/or gel formers can also be used.

The invention is further characterised in that the viscosity of the shellac solution or shellac dispersion depends on the concentration of the shellac, as already mentioned above. Preferably, shellac solutions or dispersions range from 200 to 2,500 cP·s, in particular 500 to 2,500 cP·s. A particularly preferred range is between 1,000 and 2,000 cP·s. With concentrations of approx. 55 to 60% with the new water-soluble shellac dispersions, viscosities of approx. 100,000 Mpa·s are achieved. This means that the highly concentrated dispersions with a content of about 45 to 60% wt have a cream-like to paste-like consistency but can easily be processed in this form too.

The solution or dispersion according to the invention can be used as a water-based paint or lacquer, in the manufacture of chocolate, sweets etc. It can also be used in cosmetic emulsions or gels, e.g. to improve water resistance of such products.

Below, the invention is illustrated in more detail by means of examples. All percentage information refers to weight (mass).

EXAMPLE 1

In 100 ml water, the pH value was set to 3.3 by stirring and adding citric acid. Then 1.3 g of polyvinyl pyrrolidone (PVPK30®) and 0.6 g guar hydroxypropyltrimonium chloride (CTFA name) (Jaguar C14S®) was added while further stirring took place. 15 g of purified de-waxed particle-shaped shellac was added to the solution obtained at approx. 13–15° C. at less than 1,000 rev/min, and the solution was homogenised at 1,450 rev/min.

The viscosity of the shellac solution produced in this way was 540 Mga·s.

EXAMPLE 2

The procedure was the same as in example 1, except that the pH value was 2.8 and 33 g of shellac was added. The viscosity of the solution obtained was 1,720 Mpa·s.

EXAMPLE 3

The procedure was the same as in example 1, except that 2.2 g of PVPK and 0.75 g of Jaguar C14S were used, that the pH value was set to 3.1 and that 53 g of shellac was added. A paste-like dispersion with a viscosity of 92,500 Mpa·s was obtained.

What is claimed is:

1. An aqueous shellac solution or dispersion, which comprises a content of:

Shellac of 1 to 60% wt;

at least one water-soluble film former of 0.1 to 3% wt;

at least one acid-resistant gel former of 0.1 to 1% wt;

water to 100% weight; and a pH value of 2 to 4.2.

2. A shellac solution or dispersion according to claim 1, wherein the content of shellac ranges from 10 to 50% wt.

3. A shellac solution or dispersion according to claim 2, wherein the content of shellac ranges from 15 to 50% wt.

4. A shellac solution or dispersion according to claim 2, wherein the content of shellac ranges from 20 to 40% wt.

5. A shellac solution or dispersion according to claim 1, wherein in that the pH value ranges from 2 to 3.5.

6. A shellac solution or dispersion according to claim 1, wherein the viscosity of the solution or dispersion ranges from 200 to 2,500 Mpa·s.

7. A shellac solution or dispersion according to claim 1, wherein the viscosity of the solution or dispersion ranges from 500 to 2,500 Mpa·s.

8. A shellac solution or dispersion according to claim 7, wherein the viscosity of the solution or dispersion ranges from 1,000 to 2,000 Mpa·s.

9. A method for producing an aqueous shellac solution or dispersion, characterised in that particle-shaped shellac is added to an aqueous solution and homogenised by stirring at 10 to 1,500 rev/min at a temperature of 5 to 20° C.; said aqueous solution having a pH value of 2 to 4.2 and containing at least one water-soluble film former and at least one acid-resistant gel former.

10. A method according to claim 9, wherein a purified and dewaxed shellac is used with a molecular weight of 1,000 to 1,010.

11. A method according to claim 9, wherein the pH value is kept in the range between 3.5 and 2.

12. A method according to claim 9, wherein the particle-shaped shellac is added until the viscosity of the solution is between 200 and 2,500 Mpa·s.

13. A method according to claim 9, wherein guar hydroxypropyltrimonium chloride is added as a gel former.

14. A method according to claim 9, wherein the temperature is kept in the range of 5 to 15° C.

* * * * *